United States Patent [19]

Matsubara et al.

[11] Patent Number: 6,121,311
[45] Date of Patent: Sep. 19, 2000

[54] METHOD FOR TREATING COCAINISM

[75] Inventors: Kazuo Matsubara, Asahikawa; Yasuo Urata, Takatsuki, both of Japan

[73] Assignee: Japan Tobacco Inc., Tokyo, Japan

[21] Appl. No.: 09/301,404

[22] Filed: Apr. 28, 1999

[51] Int. Cl.[7] .................................................. A61K 31/40
[52] U.S. Cl. ............................................................ 514/423
[58] Field of Search ............................................. 514/423

[56] References Cited

U.S. PATENT DOCUMENTS

| | | | |
|---|---|---|---|
| 4,826,870 | 5/1989 | Higuchi et al. | 514/422 |
| 4,857,524 | 8/1989 | Furukawa et al. | 514/227.5 |
| 4,873,342 | 10/1989 | Tanaka et al. | 548/518 |
| 4,956,380 | 9/1990 | Toda et al. | 514/422 |
| 5,028,604 | 7/1991 | Torizuka et al. | 514/227.8 |
| 5,100,904 | 3/1992 | Toda et al. | 514/343 |
| 5,158,970 | 10/1992 | Shioiri et al. | 514/422 |
| 5,198,458 | 3/1993 | Higuchi et al. | 514/397 |
| 5,254,550 | 10/1993 | Toda et al. | 514/250 |
| 5,340,832 | 8/1994 | Toda et al. | 514/423 |
| 5,506,256 | 4/1996 | Kobayashi et al. | 514/422 |
| 5,536,737 | 7/1996 | Kobayashi et al. | 514/365 |

FOREIGN PATENT DOCUMENTS

| | | |
|---|---|---|
| 04009367 | 1/1992 | Japan . |
| 08003132 | 1/1996 | Japan . |

OTHER PUBLICATIONS

Hoffman et al., "Administration of Purified Human Plasma Cholinesterase Protects Against Cocaine Toxicity in Mice", *Journal of Toxicology—Clinical Toxicology,* 34(3), 259–266 (1996).

*Primary Examiner*—Phyllis G. Spivack
*Attorney, Agent, or Firm*—Leydig, Voit & Mayer, Ltd.

[57] ABSTRACT

A method for activating cholinesterase, comprising administering a compound having a prolyl endopeptidase inhibitory activity to treat cocainism, is disclosed.

1 Claim, 6 Drawing Sheets

METHOD FOR TREATING COCAINISM

FIELD OF THE INVENTION

The present invention relates to a method for activating cholinesterase. More particularly, the present invention relates to a method for activating cholinesterase using a compound having prolyl endopeptidase inhibitory activity and a method for treating cocainism by the activation of cholinesterase using said compound.

BACKGROUND OF THE INVENTION

Cocaine is an alkaloid contained in coca (*Erythroxylon coca*) leaves a originally came from South America. It causes intense excitation, produces a dependency, and created a serious social problem of cocainism.

Cocaine directly acts on the peripheral sensory nerve fiber to reversively paralyze the same, and shuts down production and conduction of afferent impulses.

The pharmacological actions of cocaine include local anesthesia. Cocaine is advantageous in that it readily penetrates mucous membrane and infiltrates into tissues, and that it causes vasoconstriction to retard its systemic absorption, thereby prolonging anesthesia.

The systemic effect produced by absorption is found in the central nervous system and cardiovascular system. Noticeable excitation proceeds from the upper site to the lower site in the CNS. Thus, at a lower dose, it first acts on the cerebral cortex to manifest mental uplift, the sense of increased intelligence, disappearance of fatigue, euphoria and hyperkinesis. Such condition characterized by feeling of being refreshed and possession of increased mental and physical capabilities is called cocaine drunkenness.

On the other hand, its use in higher doses causes hallucination, derangement, berserk, tremor, clonic spasm, and respiratory excitation, elevation of blood pressure and body temperature, emesis and the like, all of which are caused by stimulation of medulla oblongata, and which in turn progress into suppression (e.g., coma), suppression of respiratory and cardiac functions and suppression of reflex mechanism of spinal cord. When continuously used, psychopathic symptoms such as anxiety, agrypnia, hallucination, delusion, derangement and the like, and physical symptoms of mydriasis, tachycardia, fervescence, convulsion and the like are observed. The mydriasis is also caused by peripheral(sympathetic) action of cocaine. Associated with such psychopathic symptoms, cocaine is classified as a narcotic.

As a narcotic, cocaine is characterized by the fact that it seldom shows physical dependency but shows extremely strong psychological dependency.

In a low or medium dose, its action on the cardiac function is secondary, resulting from its primary action on central and peripheral nerves. When a higher dose is intravenously administered, however, it may directly act on the myocardium to cause cardiac dysfunction. There have been also found central and peripheral actions on blood vessels. It inhibits catecholamine uptake at the adrenergic nerve ending and enhances action of norepinephrine on the vascular wall.

A cholinesterase is an enzyme which hydrolyzes choline ester into choline and organic acid. There exist two types of the enzyme in the living body; acetylcholinesterase (true cholinesterase; EC 3.1.1.7) and cholinesterase (serum cholinesterase, pseudocholinesterase; EC 3.1.1.8). The former resides in the nerve tissues, muscles, erythrocytes and the like, and specifically decomposes acetylcholine. The latter is synthesized in the liver and secreted into serum. While its biological role has not been fully elucidated, it decomposes, besides acetylcholine, various choline esters and non-choline esters.

The metabolism of cocaine is complicated, since it depends on various enzyme activities, doses and administration routes. The major metabolites are three compounds; norcocaine, benzoylecgonine and ecgonine methylester.

Given a report on the use of an organophosphate insecticide (cholinesterase inhibitor) for prolongation of cocaine excitement and a report which indicates that the metabolism of cocaine is shifted largely toward benzoylecgonine, but also somewhat toward norcocaine at low cholinesterase activity, Hoffman et al. documented a report which concludes, "when plasma cholinesterase activity is low, 1) metabolism of cocain is slowed and its toxicity is prolonged, 2) metabolism of cocain is shunted away from the nontoxic ecgonine methylester and toward the active metabolite norcocaine or potentially active metabolite benzoylecgonine." They conclude that the both mechanisms in combination enhance cocaine toxicity and that, by reference to recent findings, serum cholinesterase activity is considered to be an important determinant of cocaine toxicity (Journal of Toxicology, Clinical Toxicology, 34 (3), 259–266 (1996)). Therefore, once the serum cholinesterase activity can be improved, the above-mentioned problems will be solved, and the treatment of cocainism will be facilitated.

The present inventors have surprisingly found that a compound having a prolyl endopeptidase inhibitory activity can specifically activate the serum cholinesterase activity. Hence, administration of a compound having a prolyl endopeptidase inhibitory activity to patients will lead to the cure of cocainism.

SUMMARY OF THE INVENTION

The inventive method for activating cholinesterase and a treatment method of cocainism are characterized by the use of a compound having a prolyl endopeptidase inhibitory activity, and specifically include the following (1) to (8).

(1) A method for activating cholinesterase, comprising using a compound having a prolyl endopeptidase inhibitory activity.

(2) The method for activating cholinesterase of (1) above, wherein the compound having a prolyl endopeptidase inhibitory activity is represented by the formula [I]

wherein:

$R^1$ is a hydrogen atom, a lower alky, a phenoxy, an adamantyl, a hetero ring optionally substituted by a lower alkyl, a halogen atom, a hydroxy, a lower alkoxy, an amino, a nitro, a trifluoromethyl or an oxo, a group of the formula wherein $R^3$ is a hydrogen atom, a halogen atom, a lower alkyl, a hydroxy, a lower alkoxy, an amino or a trifluoromethyl, or a group of the formula wherein $R^4$ is a hydrogen atom, a halogen atom, a lower alkyl, a lower alkoxy, an amino or a nitro, $R^5$ is a hydrogen atom or a lower alkyl, A is a methylene, an ethylene or a propylene, and ------- shows a single bond or a double bond;

$R^2$ is a hydrogen atom, a carboxyl, a lower alkoxycarbonyl, a formyl, a hydroxymethyl, wherein $R^6$ is a hydrogen atom, a lower alkyl, an acyl, a group of the formula wherein ring D is a benzene ring or a hetero ring, $R^7$ and $R^8$ are the same or different and each is a hydrogen atom, a halogen atom, a lower alkyl optionally substituted by fluorine atom, a hydroxy, a lower alkoxy, an amino or a nitro, $R^7$ and $R^8$ may in combination form a saturated or unsaturated 5- or 6-membered ring, and p is an integer of 0 or 1–3, B is an oxygen atom, a sulfur atom, a sulfinyl, a sulfonyl, NH or a single bond, and n is an integer of 1–6, or a group of the formula wherein $R^9$ is a hydrogen atom, a halogen atom or an acyloxy, and $R^{10}$ is a diphenylmethyl, a trityl, a lower alkyl optionally substituted by a halogen atom or a group of the formula wherein $R^{11}$ and $R^{12}$ are the same or different and each is a hydrogen atom, a halogen atom or a lower alkoxy, or wherein $R^{13}$, $R^{14}$ and $R^{15}$ are the same or different and each is a lower alkyl or a phenyl;

U is an oxygen atom, a sulfur atom, a carbonyl, —$CHR^{16}$— wherein $R^{16}$ is a hydrogen atom or a lower alkoxycarbonyl, —$NR^{17}$— wherein $R^{17}$ is a hydrogen atom, an alkyl having 1 to 8 carbon atoms, a cycloalkyl having 3 to 7 carbon atoms, a phenyl, a benzyl, an acyl or a lower alkoxycarbonyl, or a single bond;

V is an oxygen atom, —$CHR^{18}$— wherein $R^{18}$ is a hydrogen atom or a hetero ring, —$NR^{19}$— wherein $R^{19}$ is a hydrogen atom or a lower alkoxycarbonyl lower alkyl, or a single bond;

W is wherein $R^{20}$ is a hydrogen atom or a lower alkyl, $R^{21}$ is a hydrogen atom, a lower alkyl or —$(CH_2)_r$—$R^{22}$ wherein $R^{22}$ is a hydrogen atom, a branched alkyl having 3 to 5 carbon atoms, a lower alkylthio, a phenyl, a phenyl substituted by hydroxy, benzyloxyphenyl, hydroxy, lower alkoxy, benzyloxy, amino, benzyloxycarbonylamino, carboxyl, benzyloxycarbonyl, indolyl, imidazolyl, or a bond of carbon atom and nitrogen atom together with $R^{20}$ and r is an integer of 0 or 1–8, and Y is a methylene or a sulfur atom, an alkylene having 1 to 8 carbon atoms, an alkenylene having 2 to 8 carbon atoms or a saturated hydrocarbon ring having 3 to 7 carbon atoms;

X is a methylene or a sulfur atom; and m is an integer of 0 or 1–8.

(3) The method for activating cholinesterase of (2) above, wherein the compound having the prolyl endopeptidase inhibitory activity is a compound of the formula [I] wherein $R^1$ is a methyl, a hetero ring or wherein $R^{3\prime}$ is a hydrogen atom, a halogen atom, a lower alkyl, a hydroxy, a lower alkoxy or an amino; $R^2$ is wherein $R^{6\prime}$ is a hydrogen atom or an acyl and n' is an integer of 1–4;

U is an oxygen atom, a sulfur atom, —$CHR^{16}$— wherein $R^{16}$ is as defined at above, or —$NR^{17\prime}$— wherein $R^{17\prime}$ is a hydrogen atom or a lower alkoxycarbonyl;

V is an oxygen atom, —$CHR^{18}$— wherein $R^{18}$ is as defined above, —$NR^9$— wherein $R^{19}$ is as defined above; and

W is wherein Y is as defined above; and m is an integer of 0 or 1–6.

(4) The method for activating choline sterase of (1) above, wherein the compound having the prolyl endopeptidase inhibitory activity is represented by the formula [II]

[II]

wherein $R^{23}$ is a lower alkyl and E is a protecting group of N-terminal in the amino acid chemistry or an acyl of an amino acid having a protecting group at the N-terminal.

(5) The method for activating cholinesterase of (3) above, wherein the compound having the prolyl endopeptidase inhibitory activity is (2S)-1-benzylaminocarbonyl-[(2S)-2-glycolylpyrrolidinyl]-2-pyrrolidinecarboxamide.

(6) A method for treating cocainism, comprising administering a pharmaceutically effective amount of a compound having a prolyl endopeptidase inhibitory activity.

(7) The method for treating cocainism according to (6) above, wherein the compound having the prolyl endopeptidase inhibitory activity is a compound of the formula [I].

(8) The method for treating cocainism according to (7) above, wherein the compound having the prolyl endopeptidase inhibitory activity is a compound of the formula [I] wherein $R^1$ is a methyl, a hetero ring or wherein $R^{3\prime}$ is a hydrogen atom, a halogen atom, a lower alkyl, a hydroxy, a lower alkoxy or an amino; $R^2$ is wherein $R^{6\prime}$ is a hydrogen atom or an acyl and n' is an integer of 1–4; U is an oxygen atom, a sulfur atom, —$CHR^{16}$— wherein $R^{16}$ is as defined above, or —$NR^{17\prime}$— wherein $R^{17\prime}$ is a hydrogen atom or a lower alkoxycarbonyl; V is an oxygen atom, —$CHR^{18}$— wherein $R^{18}$ is as defined above, or —$NR^{19}$— wherein $R^{19}$ is as defined above; W is wherein Y is as defined above; and m is an integer of 0 or 1–6.

(9) The method for treating cocainism according to (6) above, wherein the compound having the prolyl endopeptidase inhibitory activity is a compound of the formula [II].

(10) The method for treating cocainism according to (8) above, wherein the compound having the prolyl endopeptidase inhibitory activity is (2S)-1-benzylaminocarbonyl-[(2S)-2-glycolylpyrrolidinyl]-2-pyrrolidine-carboxamide.

DETAILED DESCRIPTION OF THE INVENTION

The compound having a prolyl endopeptidase inhibitory activity in the present invention includes any compound having inhibitory activity on an enzyme called prolyl endopeptidase. A first example of such compound is a compound having the above-mentioned formula [I], which specifically exemplified by the following compounds. Note that m and n designating an integer in the following formulas [I-a] to [I-j] are used solely in the context of the corresponding formula.

The compound disclosed in U.S. Pat. No. 5,536,737, which is represented by the formula [I-a]:

[I-a]

wherein $R^a$ is a hydrogen atom or an acyl; $U^a$ is —O—, —$CHR^{1a}$— wherein $R^{1a}$ is a hydrogen atom or a hetero ring, or —$NR^{2a}$— wherein $R^{2a}$ is a hydrogen atom or a lower alkoxycarbonyl lower alkyl; $V^a$ is —O—, —S—, —$CHR^{3a}$— wherein $R^{3a}$ is a hydrogen atom or a lower alkoxycarbonyl or —$NR^{4a}$— wherein $R^{4a}$ is a hydrogen atom, a lower alkyl or an acyl; Wa is a methyl, a hetero ring or wherein $R^{5a}$ is a hydrogen atom, a halogen atom, a lower alkyl, an amino, a hydroxy or a lower alkoxy;

$X^a$ and $Y^a$ are the same or different and each is —$CH_2$— or —S—;

m is an integer of 0–6; and n is an integer of 1–4.

Examples of the compound of the formula [I-a] include (S)-2-[[(S)-2-(acetoxyacetyl)-1-pyrrolidinyl]carbonyl]-N-(phenylmethyl)-1-pyrrolidinecarboxamide, (S)-2-[[(S)-2-(hydroxyacetyl)-1-pyrrolidinyl]carbonyl]-N-(phenylmethyl)-1-pyrrolidinecarboxamide, (S)-2-[[(S)-2-(benzoyloxyacetyl)-1-pyrrolidinyl]carbonyl]-N-(phenylmethyl)-1-pyrrolidinecarboxamide and the like.

The compound disclosed in U.S. Pat. No. 5,506,256, which is represented by the formula [I-b]:

[I-b]

wherein:

$A^b$ is or a single bond;

$B^b$ is

$W^b$ is or $CH_3$— where $R^{1b}$ is a hydrogen atom, a halogen atom or a lower alkoxy;

$X^b$ is —S—, —SO—, —SO2—, —O— or —NH—;

$R^b$ is or a lower alkyl having 1 to 5 carbon atoms where l is an integer of 0 to 3, $Y^b$ and $Z^b$ are the same or different and each is a hydrogen atom, a halogen atom, a lower alkyl having 1 to 5 carbon atoms which may be substituted by fluorine atoms, a nitro, a hydroxy or a lower alkoxy, and $Y^b$ and $Z^b$ may combinedly form a saturated or unsaturated 5- or 6-membered ring selected from the group consisting of furan ring, oxolane ring, 1,3-dioxolane ring, thiophene ring, pyrrole ring, pyrrolidine ring, oxane ring, pyridine ring and benzene ring; and n is an integer of 1 to 6.

Examples of the compound of the formula [I-b] include (2S)-1-(N-benzylaminocarbonyl-L-prolyl)-2-(phenoxyacetyl)pyrrolidine, (2S)-1-(N-benzyloxycarbonyl-L-prolyl)-2-[(phenylthio)acetyl]pyrrolidine, (2S)-1-(N-benzyloxycarbonyl-L-prolyl)-2-[1-hydroxy-2-(phenylsulfonyl)ethyl]pyrrolidine and the like.

The compound disclosed in U.S. Pat. No. 5,506,256, which is represented by the formula [I-c]:

[I-c]

wherein:

$A^c$ is —O—, —$CHR^{1c}$— or —$NR^{2c}$— (wherein $R^{1c}$ is a hydrogen atom or a hetero ring, and $R^{2c}$ is a lower alkoxycarbonyl(lower)alkyl;

$B^c$ is or —$NR^{3c}$—$CHR^{4c}$— (wherein $R^{3c}$ and $R^{4c}$ are the same or different, and each is a hydrogen atom or a lower alkyl);

$W^c$ is a phenyl which may be substituted by at least one substituent selected from the group consisting of a halogen atom, a lower alkyl and a lower alkoxy, an adamantyl, a lower alkyl and a hetero ring;

$U^c$ is —O—, —S—, —NH— or —CHR$^{5c}$— (wherein R$^{5c}$ is a hydrogen atom or a lower alkoxycarbonyl);

$X^c$ is —S—, —SO—, —SO$_2$—, —O— or —NH—; and $R^c$ is (wherein $D^c$ is a benzene ring or a hetero ring, $Y^c$ and $Z^c$ are the same or different and each is a hydrogen atom, a halogen atom, a lower alkyl which may be substituted by at least one fluorine atom, amino, nitro, hydroxy or a lower alkoxy)

with the proviso that when $U^c$ is —CH$_2$—, at least $W^c$ is adamantyl or a hetero ring, or $A^c$ is —CHR$^{1c}$— or —NR$^{2c}$— (wherein R$^{1c}$ is a hetero ring and R$^{2c}$ is a lower alkoxycarbonyl(lower)alkyl), $B^c$ is thiazolidine, or $R^c$ is a hetero ring.

Examples of the compound of the formula [I-c] include (2S)-2-(4-methoxyphenoxyacetyl)-1-[N-[(phenylthio) acetyl]-L-prolyl]pyrrolidine, (2S)-1-[N-(benzylaminocarbonyl)-L-thioprolyl]-2-(phenoxyacetyl) pyrrolidine, (2S)-1-[N-[N-benzyl-N-(ethoxycarbonylmethyl)aminocarbonyl]-L-prolyl]-2-(phenoxyacetyl)pyrrolidine and the like.

The compound disclosed in Japanese Patent Unexamined Publication No. 3132/1996, which is represented by the formula [I-d]:

[I-d]

wherein $R^{1d}$ is an optionally substituted aryl or an optionally substituted heteroaryl; $R^{2d}$ is a hydrogen atom, a halogen atom or an acyloxy; $R^{3d}$ is a carboxyl-protecting group; $A^d$ is an oxygen atom, NH or CH$_2$; and n is an integer of 1–3.

Examples of the compound of the formula [I-d] include (S)-2-[[(S)-2-[(2R,S)-2-acetoxy-2-(ethoxycarbonyl)acetyl]-1-pyrrolidinyl]carbonyl]-N-(phenylmethyl)-1-pyrrolidinecarboxamide, (S)-2-[[(S)-2[(2R,S)-2acetoxy-2-(benzyloxycarbonyl)acetyl]-1-pyrrolidinyl]carbonyl]-N-(phenylmethyl)-1-pyrrolidinecarboxamide and the like.

The compound disclosed in U.S. Pat. No. 4,873,342, which is represented by the formula [I-e]:

[I-e]

wherein m is an integer of 1–8; n is an integer of 1–6; $R^{1e}$ is a hydrogen atom; $R^{2e}$ is a hydrogen atom, a branched alkyl having 3 to 5 carbon atoms, a phenyl, a hydroxyphenyl, an indolyl, an imidazolyl or a methylthio; or $R^{1e}$ and $R^{2e}$ combinedly show a carbon-nitrogen bond; and $R^{3e}$ is a lower alkyl ester, a hydroxymethyl or a formyl.

Examples of the compound of the formula [I-e] include N-[N-(4-phenylbutanoyl)norleucyl]-prolinal, N-[N-(4-phenylbutanoyl)phenylalanyl]-prolinal, N-[N-(4-phenylbutanoyl)methionyl]-prolinal and the like.

The compound disclosed in U.S. Pat. Nos. 4,826,870 and 5,198,458, which is represented by the formula [I-f]:

[I-f]

wherein m is an integer of 0 or 1–7; n is an integer of 0 or 1–8; $R^f$ is a phenyl, a substituted phenyl, a phenoxy or a substituted phenoxy; $R^{1f}$ is a hydrogen atom; $R^{2f}$ is a hydrogen atom, a branched alkyl having 3 to 5 carbon atoms, a phenyl, a hydroxyphenyl, a benzyloxyphenyl, an alkylthio containing an alkyl having 1 to 3 carbon atoms, an amino, a benzyloxycarbonylamino, a carboxyl, a carboxylic acid benzyl ester group, a hydroxy, a benzyloxy, an indolyl or an imidazolyl; or $R^{1f}$ and $R^{2f}$ combinedly show a carbon-nitrogen bond; provided that when m is 0, $R^f$ is arylalkyloxy having 7 to 9 carbon atoms and $R^{1f}$ and $R^{2f}$ combinedly show a carbon-nitrogen bond.

The compound of the formula [I-f] includes, for example, N-(γ-phenyl)butanoyl-L-valyl-pyrolidinimide, N-(γ-phenyl)butanoyl-L-leucyl-pyrrolidinimide and the like.

The compound disclosed in U.S. Pat. No. 4,857,524, which is represented by the formula [I-g]:

[I-g]

wherein is a 5- or 6-membered saturated hetero ring which may include hetero atom other than N; and $R^g$ is a hydrogen atom or an alkoxycarbonyl.

Examples of the compound of the formula [I-g] include 3-[(R)-(—)-3-carbobenzoxythiazolidine-4-carbonyl] thiazolidine, 3-[(R)-(—)-3-carbobenzoxythiazolidine-4-carbonyl]pyrrolidone and the like.

The compound disclosed in U.S. Pat. Nos. 4,956,380, 5,100,904, 5,254,550 and 5,340,832, which is represented by the formula [I-h]:

wherein $A^h$ is an alkylene having 1 to 8 carbon atoms, an alkenylene having 2 to 8 carbon atoms or a saturated hydrocarbon ring having 3 to 7 carbon atoms; $R^h$ is a hydrogen atom, a phenyl, a benzyl, an alkyl having 1 to 8 carbon atoms or a cycloalkyl having 3 to 7 carbon atoms; $B^h$ is a single bond or an alkylene having 1 to 8 carbon atoms which may be substituted by phenyl or benzyl; and $D^h$ is a carbon ring or hetero ring which is unsubstituted or substituted by 1 to 3 member(s) selected from halogen atom, alkyl, alkoxy having 1 to 4 carbon atoms, nitro and trifluoromethyl.

Examples of the compound of the formula [I-h] include N-[3-[N-(2-phenylethyl)carbamoyl]propanoyl]-L-prolinal, N-[3-(N-benzylcarbamoyl)-propanoyl]-L-prolinal, N-[3-[N-(4-chlorophenylmethyl)-N-phenylcarbamoyl]propanoyl-L-prolinal and the like.

The compound disclosed in U.S. Pat. No. 5,028,604, which is represented by the formula [I-i]:

wherein $A^i$ is a methylene, an ethylene or a propylene; $B^i$ is a methylene or an ethylene; m is an integer of 0–5; $X^i$ and $Y^i$ are different and each is a methylene or a sulfur atom; $R^{1i}$ is a hydrogen atom, a carboxyl, a lower alkyl ester, a hydroxymethyl or a formyl; $R^{2i}$ is a hydrogen atom, a halogen atom, a lower alky, a lower alkoxy, a nitro or an amino; $R^{3i}$ is a hydrogen atom or a lower alkyl; and ------ is a single bond or a double bond.

Examples of the compound of the formula [I-i] include methyl 1-(2-indanylacetyl)-L-prolinate, 1-[3-(2-indanylacetyl)-L-thioprolyl]pyrrolidine and the like.

The compound disclosed in Japanese Patent Unexamined Publication No. 9367/1992, which is represented by the formula [I-j]:

wherein $A^j$ is a thienyl, a benzofuranyl, a benzothiophenyl, an indolyl, a 2,3-dihydrobenzofuranyl, a chromanyl, a 4,5, 6,7-tetrahydrobenzothiophenyl, a 4,5,6,7-tetrahydrobenzofuranyl or a 1-oxoindanyl; m is an integer of 0–5; and $X^j$ and $Y^j$ are the same or different and each is a methylene or a sulfur atom.

Examples of the compound of the formula [I-j] include 1-(thiophen-2-ylcarbonyl)-L-thioproline and the like.

A second example of the compound having a prolyl endopeptidase inhibitory activity is a compound of the above-mentioned formula [II] which is exemplified by the compound disclosed in U.S. Pat. No. 5,158,970 having the formula [II-k]:

wherein $R^k$ is a lower alkyl; and $X^k$ is a protecting group at the N-terminal in amino acid chemistry or acyl of an amino acid having a protecting group at the N-terminal.

Examples of the compound of the formula [II-k] include p-methoxybenzoyl-L-prolynal dimethylacetal, N-benzyloxycarbonyl-L-prolyl-L-prolinal diethylacetal and the like.

As used herein, lower alkyl is a linear or branched alkyl having 1 to 6 carbon atoms, which is exemplified by methyl, ethyl, propyl, isopropyl, butyl, isobutyl, sec-butyl, tert-butyl, pentyl, isopentyl, neopentyl, hexyl, isohexyl, neohexyl and the like, with preference given to a linear or branched alkyl having 1 to 4 carbon atoms which is specifically methyl, ethyl, propyl, isopropyl, butyl, isobutyl, sec-butyl, tert-butyl and the like.

The lower alkyl of "lower alkyl having 1 to 5 carbon atoms" and "lower alkyl having 1 to 5 carbon atoms which may be substituted by fluorine atom" is exemplified by the above-mentioned lower alkyl having 1 to 5 carbon atoms, such as methyl, ethyl, propyl, isopropyl, butyl, isobutyl, sec-butyl, tert-butyl, pentyl, isopentyl, neopentyl and the like. Examples of the lower alkyl having 1 to 5 carbon atoms which is substituted by fluorine atom include trifluoromethyl, difluoromethyl, fluoromethyl and the like.

The lower alkyl of "lower alkyl optionally substituted by at least one fluorine atom" and the lower alkyl of "lower alkyl optionally substituted by halogen atom" are the same as those defined above. The lower alkyl substituted by at least one fluorine atom may be, for example, trifluoromethyl, difluoromethyl, fluoromethyl and the like; and lower alkyl substituted by halogen atom may be, for example, 2,2,2-trichloroethyl, 2-chloroethyl, 3-chloropropyl and the like.

The branched alkyl having 3 to 5 carbon atoms means, for example, isopropyl, isobutyl, sec-butyl, tert-butyl, isopentyl, neopentyl, tert-pentyl and the like.

The alkyl having 1 to 8 carbon atoms is a linear or branched alkyl having 1 to 8 carbon atoms, which is specifically methyl, ethyl, propyl, butyl, pentyl, hexyl, heptyl, octyl, isomers thereof and the like.

The cycloalkyl having 3 to 7 carbon atoms is specifically cyclopropyl, cyclobutyl, cyclopentyl, cyclohexyl, cycloheptyl and the like.

The alkylene having 1 to 8 carbon atoms is a linear or branched alkylene having 1 to 8 carbon atoms, which is specifically methylene, ethylene, trimethylene, tetramethylene, pentamethylene, hexamethylene, heptamethylene, octamethylene and isomers thereof, with preference given to those having 1 to 4 carbon atoms. The alkylene of "alkylene having 1 to 8 carbon atoms which is optionally substituted by phenyl or benzyl" is as defined above.

The alkenylene having 2 to 8 carbon atoms is the above-mentioned alkylene but not methylene, and has an optional number of double bond. Preferred are those having one double bond and 2 to 4 carbon atoms.

The saturated hydrocarbon ring having 3 to 7 carbon atoms is specifically cyclopropane, cyclobutane, cyclopentane, cyclohexane, cycloheptane, cyclooctane and the like.

The halogen atom is fluorine atom, chlorine atom, bromine atom, iodine atom and the like.

The lower alkoxy is a linear or branched alkoxy having 1 to 6 carbon atoms, which is specifically methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, neohexyloxy and the like, with preference given to a linear or branched alkoxy having 1 to 4 carbon atoms. Specific examples thereof include methoxy, ethoxy, propoxy, isopropoxy, butoxy, isobutoxy, sec-butoxy, tert-butoxy and the like.

The lower alkylthio is a linear or branched alkylthio having 1 to 6 carbon atoms, which is specifically methylthio, ethylthio, propylthio, isopropylthio, butylthio, isobutylthio, sec-butylthio, tert-butylthio, pentylthio, isopentylthio, neopentylthio, tert-pentylthio, hexylthio, isohexylthio, neohexylthio and the like, with preference given to a linear or branched alkylthio having 1 to 4 carbon atoms. Specific examples thereof include methylthio, ethylthio, propylthio, isopropylthio, butylthio, isobutylthio, sec-butylthio, tert-butylthio and the like. The alkylthio containing alkyl having 1 to 3 carbon atoms is exemplified by methylthio, ethylthio, propylthio, isopropylthio and the like.

The alkoxycarbonyl is specifically methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl, isohexyloxycarbonyl, neohexyloxycarbonyl and the like, with preference given to alkoxycarbonyl having 2 to 5 carbon atoms. Specific examples thereof include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and the like. The lower alkoxycarbonyl means those having 2 to 7 carbon atoms.

The lower alkoxycarbonyl lower alkyl is the above-mentioned alkyl having 1 to 5 carbon atoms which is substituted by lower alkoxycarbonyl. Examples thereof include methoxycarbonylmethyl, 2-(methoxycarbonyl)ethyl, 3-(methoxycarbonyl)propyl, ethoxycarbonylmethyl, 2-(ethoxycarbonyl)ethyl, 3-(ethoxycarbonyl)propyl, propoxycarbonylmethyl, 2-(propoxycarbonyl)ethyl, 3-(propoxycarbonyl)propyl and the like.

The acyl is a linear or branched alkanoyl having 1 to 6 carbon atoms; (hetero)arylcarbonyl having 3 to 11 carbon atoms, which may have hetero atom selected from oxygen, nitrogen and sulfur; or (hetero)arylalkanoyl having 4 to 14 carbon atoms, which may have hetero atom selected from oxygen, nitrogen and sulfur. Examples of alkanoyl include formyl, acetyl, propionyl, isopropionyl, butyryl, isobutyryl, pivaloyl, valeryl, isovaleryl, caproyl, isocaproyl and the like. Examples of (hetero)arylcarbonyl include benzoyl, naphthoyl, nicotinoyl, isonicotinoyl, thenoyl, furoyl, pyrrolylcarbonyl, pyrazolylcarbonyl, imidazolylcarbonyl, pyrazinylcarbonyl, pyrimidinylcarbonyl, triazolylcarbonyl, thiazolylcarbonyl, benzofuranylcarbonyl, indolylcarbonyl, benzotriazolylcarbonyl and the like. Examples of (hetero)arylalkanoyl include phenylacetyl, phenylpropionyl, naphthylacetyl, naphthylpropionyl, pyridylacetyl, thienylacetyl, thienylbutyryl, imidazolylacetyl, thiazolylacetyl, indolylacetyl, indolylpropionyl and the like. Preferred are alkanoyl having 2 to 5 carbon atoms, such as acetyl, propionyl, isopropionyl, butyryl, isobutyryl, pivaloyl, valeryl and isovaleryl; (hetero)arylcarbonyl having 4 to 7 carbon atoms, which may have a hetero atom selected from oxygen, nitrogen and sulfur, such as benzoyl, naphthoyl, nicotinoyl, isonicotinoyl, thenoyl, furoyl, pyrrolylcarbonyl, pyrazolylcarbonyl, imidazolylcarbonyl, pyrazinylcarbonyl, pyrimidinylcarbonyl and thiazolylcarbonyl; and (hetero)arylalkanoyl having 5 to 9 carbon atoms, which may have a hetero atom selected from oxygen, nitrogen and sulfur, such as phenylacetyl, phenylpropionyl, pyridylacetyl, thienylacetyl, thienylbutyryl, imidazolylacetyl and thiazolylacetyl, with particular preference given to alkanoyl having 2 to 5 carbon atoms (e.g., acetyl, propionyl, isopropionyl, butyryl, isobutyryl and pivaloyl); arylcarbonyl having 4 to 7 carbon atoms (e.g., benzoyl and the like); and arylalkanoyl having 5 to 9 carbon atoms (e.g., phenylacetyl and phenylpropionyl). The above-mentioned (hetero)arylcarbonyl and (hetero)arylalkanoyl may have 1 to 3 substituent(s) on the (hetero)aryl, and the substituent is exemplified by halogen atom, lower alkyl, amino, hydroxy, lower alkoxy, carboxy, lower alkoxycarbonyl, acyl and the like.

The acyloxy is an acyloxy having 1 to 6 carbon atoms, which is optionally substituted by halogen atom. Examples thereof include formyloxy, acetyloxy, propionyloxy, butyryloxy, valeryloxy, pivaloyloxy, chloroacetyloxy, trichloroacetyloxy, trifluoroacetyloxy, benzoyloxy and the like, with preference given to acetyloxy, pivaloyloxy and benzoyloxy, and particular preference given to acetyloxy.

The hetero ring in this specification means a saturated or unsaturated optionally condensed 4- to 7-membered ring having 1 to 3 hetero atom(s) selected from oxygen, nitrogen and sulfur, which is exemplified by azetidine, pyrrole, pyrroline, pyrrolidine, furan, dihydrofuran, tetrahydrofuran, tetrahydrofuran(oxolane), 1,3-dioxolane, tetrahydropyran (oxane), thiophene, dihydrothiophene, tetrahydrothiophene, imidazole, imidazoline, imidazolidine, pyrazole, pyrazoline, pyrazolidine, oxazole, oxazolidine, isoxazole, isoxazolidine, thiazole, thiazolidine, isothiazole, isothiazolidine, furazan, pyridine, pyrimidine, pyrazine, piperidine, piperazine, morpholine, homopiperidine, benzofuran, 2,3-dihydrobenzofuran, 4,5,6,7-tetrahydrobenzofuran, benzothiophene, 2,3-dihydrobenzothiophene, 4,5,6,7-tetrahydrobenzothiophene, indole, indoline, chromene, chroman, quinoline and isoquinoline, with preference given to pyridine, piperidine and morpholine.

The saturated or unsaturated 5- or 6-membered ring in this specification means, for example, cycloheptane, cycloheptene, cycloheptdiene, cyclohexane, cyclohexene, cyclohexdiene, benzene, pyrrole, pyrroline, pyrrolidine, furan, dihydrofuran, tetrahydrofuran, thiophene, dihydrothiophene, tetrahydrothiophene, imidazole, imidazoline, imidazolidine, pyrazole, pyrazolidine, oxazole, oxazolidine, isoxazole, isoxazolidine, thiazole, thiazolidine, isothiazole, isothiazolidine, furazan, pyridine, pyrimidine, pyrazine, dihydropyridine, piperidine, piperazine, morpholine and the like.

The hetero atom in the hetero ring of "5- or 6-membered saturated heterocyclic ring which may include hetero atom other than N" is exemplified by O, S and the like. The saturated heterocyclic ring of 5- or 6-membered ring is exemplified by those recited for the above-mentioned hetero ring.

The protecting group at the N-terminal in amino acid chemistry is specifically methoxybenzoyl, methoxyphenylbutyryl, tert-butyryl and the like.

The amino acid of "acyl of an amino acid" is exemplified by proline, sarcosine, pyroglutamic acid and the like; and the protecting group at the N-terminal of "acyl of an amino acid having a protecting group at the N-terminal" is exemplified by p-toluenesulfonyl, benzyloxycarbonyl, benzyloxysuccinyl, succinyl and the like. The amino acid of "acyl of an amino acid having a protecting group at the N-teriinal" is exemplified by N-benzyloxycarbonylproline, N-benzyloxysuccinylproline, N-p-toluenesulfonylsarcosine, N-benzyloxycarbonylsarcosine, N-benzyloxysuccinylsarcosine, N-succinylsarcosine, N-benzyloxycarbonylpyroglutamine, N-benzyloxysuccinylpyroglutamine, N-succinylpyroglutamine and the like.

The halogen atom, lower alkyl and lower alkoxy of "phenyl which may be substituted by at least one substituent selectd from the group consisting of a halogen atom, a lower alkyl and a lower alkoxy" are each as defined above.

The aryl of "optionally substituted aryl" is specifically condensed or noncondensed aromatic hydrocarbon group such as phenyl, naphthyl and indanyl, which may be partly hydrogenated or saturated on demand, such as indanyl and 1,2,3,4-tetrahydronaphthyl.

The heteroaryl of "optionally substituted heteroaryl" is specifically an optionally condensed 5- or 6-membered hetero ring having hetero atom such as nitrogen atom and sulfur atom. Examples thereof include thienyl, furyl, pyrrolyl, imidazolyl, pyrazolyl, thiazolyl, isothiazolyl, oxazolyl, isoxazolyl, furazanyl, pyridyl, pyrazinyl, pyrimidinyl, benzofuranyl, 2,3-dihydrobenzofuranyl, benzothienyl, indolyl, chromenyl, chromanyl, quinolinyl, isoquinolinyl and the like.

The substituent of "optionally substituted aryl or optionally substituted heteroaryl" is exemplified by lower alkyl (as defined above), lower alkoxy (as defined above), halogen atom (as defined above) and the like.

The carboxyl-protecting group may be any protecting group as long as it is generally used for protecting carboxyl group, and is exemplified by alkyl such as methyl, ethyl, propyl, isopropyl, butyl and isobutyl; halogen-substituted alkyl such as 2,2,2-trichloroethyl and 2,2,2-trifluoroethyl; aralkyl such as benzyl, p-methoxybenzyl, 3,4-dimethoxybenzyl, o-nitrobenzyl, p-nitrobenzyl, p-bromobenzyl, diphenylmethyl and trityl; silyl such as trimethylsilyl, triethylsilyl, isopropyldimethylsilyl, tert-butyldimethylsilyl, di-tert-butylmethylsilyl, phenyldimethylsilyl and tert-butyldiphenylsilyl; and the like.

The "lower alkyl ester group" is specifically methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and the like.

The substituent of "substituted phenyl" is exemplified by alkyl having 1 to 9 carbon atoms, benzyl, phenethyl, lower alkenyl, styryl, hydroxy, benzyloxy, phenoxy, acyl, halogen atom and the like. The substituent of "substituted phenoxy" is exemplified by those recited as the substituent for substituted phenyl.

The "arylalkyloxy having 7 to 9 carbon atoms" is exemplified by benzyloxy, phenethyloxy, phenylpropoxy and the like.

The alkyl or alkoxy having 1 to 4 carbon atoms of "a carbon ring or hetero ring which is unsubstituted or substituted by 1 to 3 member(s) selected from alkyl, alkoxy having 1 to 4 carbon atoms, nitro and trifluoromethyl" is exemplified by the above-mentioned lower alkyl and lower alkoxy having 1 to 4 carbon atoms. The carbon ring may be, for example, benzene, naphthalene, indene, azulene, fluorene, phenanthrene, anthracene, acenaphthalene, biphenylene rings and these rings partly or entirely saturated; heterocycle may be, for example, furan, thiophene, pyrrole, oxazole, isoxazole, thiazole, isothiazole, imidazole, pyrazole, furazan, pyran, pyridine, pyridazine, pyrimidine, pyrazine, indole, isoindole, benzofuran, benzothiophene, indolizine, chromene, quinoline, isoquinoline, quinolizine, purine, indazole, quinazoline, cinnoline, quinoxaline, phthalazine, pterin,carbazole, acridine, phenanthridine, xanthene, phenazine, phenothiazine and these rings partly or entirely saturated.

The compound having a prolyl endopeptidase inhibitory activity, which is suitably used in the present invention, namely, (2S)-1-benzylaminocarbonyl-[(2S)-2-glycolylpyrrolidinyl]-2-pyrrolidinecarboxamide, has the following formula.

While the dose of the compound having prolyl endopeptidase inhibitory activity to be administered in the present invention varies depending on age, body weight, symptom, therapeutic effect, kind of compound, administration route and the like, it is, in the case of the compound of the formula [I], 1 mg–100 mg per dose for an adult by oral administration once to several times a day, or 0.2 mg–20 mg per dose for an adult by parenteral administration once to several times a day.

This compound having prolyl endopeptidase inhibitory activity is used in the dosage form of a solid composition or liquid composition for oral administration; or an injection, suppository or the like for parenteral administration.

The solid composition for oral administration includes tablet, capsule, powder, granule and the like. One or more active ingredient(s) is/are admixed with at least one pharmaceutically acceptable inert diluent to give a solid composition. Where necessary, excipient, binder, lubricant, disintegrator, solubilizing agent, stabilizer and the like may be added. A capsule includes hard capsule and soft capsule.

The liquid composition for oral administration includes solution, emulsion, suspension, syrup, elixir and the like. The liquid composition contains conventional inert pharmaceutically acceptable diluents. It may also contain auxiliary agent (e.g., moistening agent), suspending agent, sweetener, flavor, aromatic and preservative.

The injection for parenteral administration may be, for example, sterile aqueous or nonaqueous solution, suspension, emulsion and the like. The injection contains one or more active ingredient(s) admixed with at least one pharmaceutically acceptable inert aqueous diluent, pharmaceutically acceptable inert nonaqueous diluent, and the like. Where necessary, antiseptic, moistening agent, emulsifying agent, dispersing agent, stabilizer, solubilizing agent and the like may be added. They are generally sterilized by filtration using a bacteria preserving filter and the like, addition of antimicrobial agents or irradiation of γ-ray. Alternatively, after these treatments, the liquid composition is prepared into a solid composition by lyophilization and the like, and diluted immediately before use with sterile water, sterile diluent for injection and the like.

The present invention is explained in more detail by illustrative Examples, to which the present invention is not limited.

EXAMPLE 1

Figure 1:
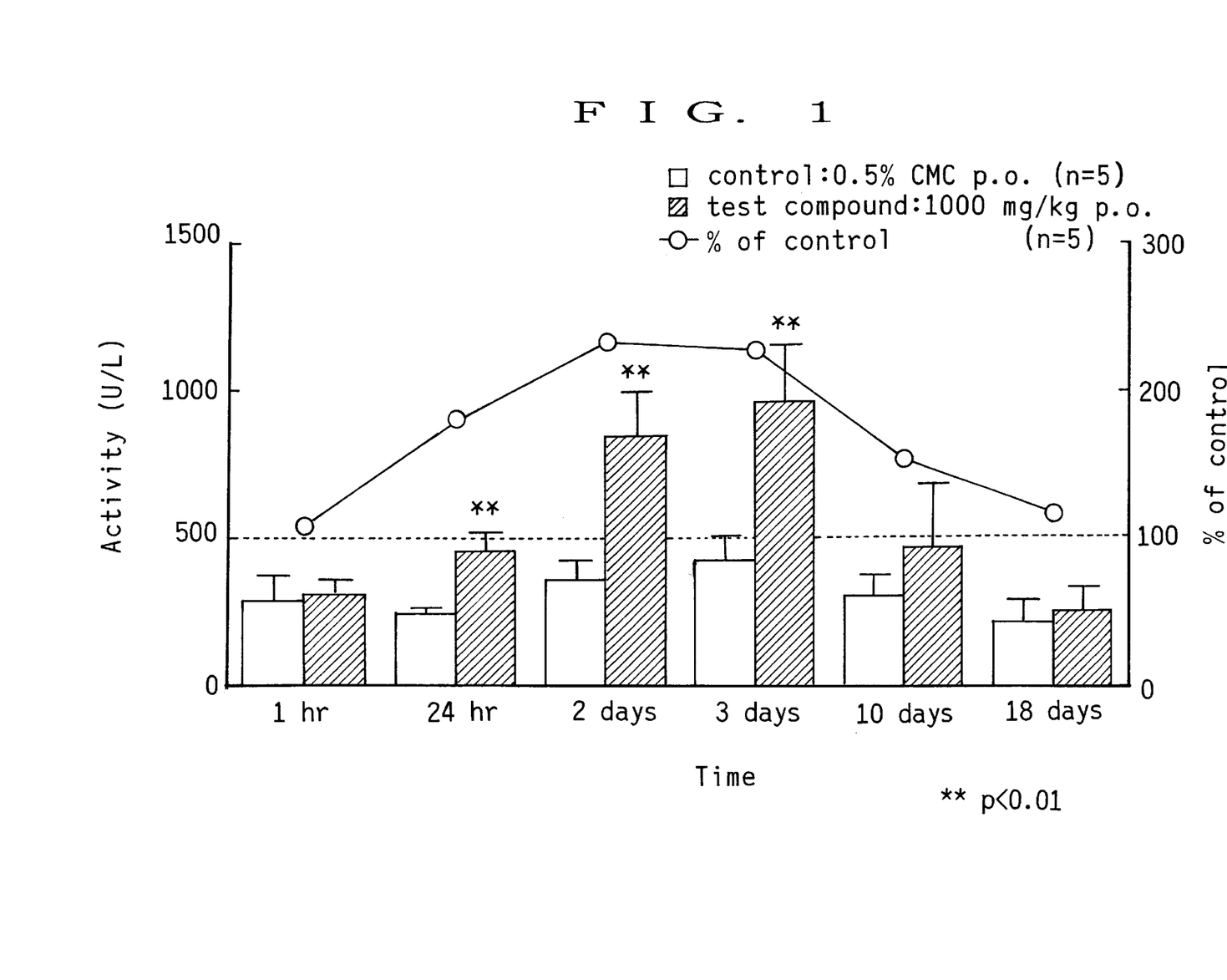
FIG. 1 shows the effects of the test compound (single oral administration) on plasma cholinesterase activity.

Time Course Changes in Plasma Cholinesterase Activity After Single Oral Administration Male SD rats (7 weeks of age, Japan Charles River, 5 per group) were orally administered with (2S)-1-benzylaminocarbonyl-[(2S)-2-glycolylpyrrolidinyl]-2-pyrrolidinecarboxamide (1000 mg/kg) suspended in 0.5% aqueous sodium carboxymethylcellulose solution (5 ml/kg). To the control group was orally administered 0.5% aqueous sodium carboxymethylcellulose solution (5 ml/kg). One hour, 24 hours, 2 days, 3 days, 10 days and 18 days later, the rats were opened in abdomen under light ether anesthesia, and blood samples were taken from the aorta into heparin-treated tubes using a blood collection needle. The blood was centrifuged for 15 min at 3000 r.p.m. and the obtained plasma was subjected to determination of cholinesterase activity according to the DTNB method of Ellman (Biochem. Pharmacol., 7, 88–95 (1961)). The activity was determined using 7.0 mM butyrylthiocholine iodide as a substrate. For the determination, a spectrophotometer was used and released thiocholine was determined by the rate assay at wavelength of 412 nm. Changes in plasma cholinesterase activity at 1 hour, 24 hours, 2 days, 3 days, 10 days and 18 days after the administration are shown in FIG. 1. The cholinesterase activity of the group administered with the test compound elevated about 1.8 times that of control at 24 hours after administration and reached about 2.3 times that of control at 2 days after administration. The cholinesterase activity gradually decreased from 3 days postadministration to the same level with the control at 18 days postadministration.

EXAMPLE 2

Figure 2:
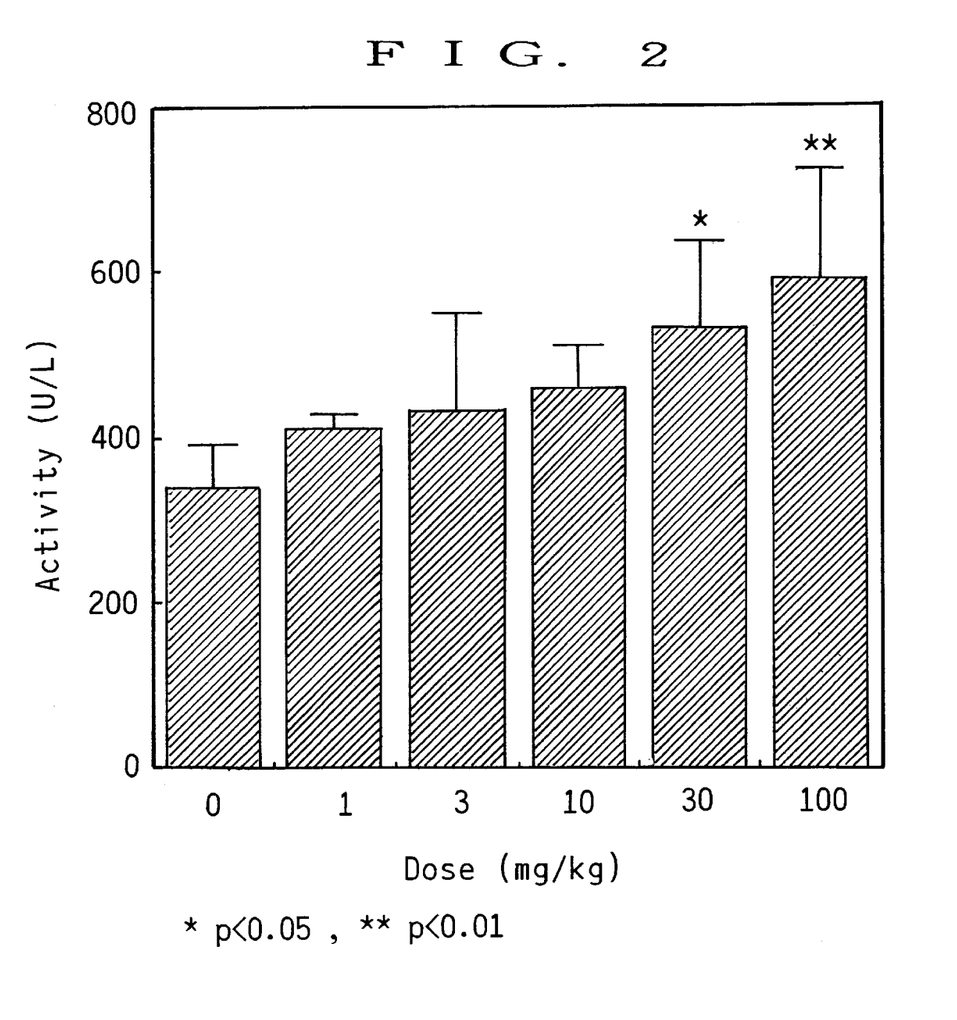
FIG. 2 shows the dose-dependent effects of the test compound (single oral administration) on plasma cholinesterase activity.

Dose Dependency of Plasma Cholinesterase Activity After Single Oral Administration Male SD rats (6 weeks of age, Japan Charles River, 5 per group) were orally administered with (2S)-1-benzylaminocarbonyl-[(2S)-2-glycolylpyrrolidinyl]-2-pyrrolidinecarboxamide (1, 3, 10, 30 and 100 mg/kg) suspended in 0.5% aqueous sodium carboxymethylcellulose solution (5 ml/kg). To the control group was orally administered 0.5% aqueous sodium carboxymethylcellulose solution (5 ml/kg). In the same manner as in Example 1, the plasma cholinesterase activity was determined at 3 days postadministration. The results are shown in FIG. 2. The cholinesterase activity showed significant increase by the administration of 30 mg/kg to 100 mg/kg of the test compound, and the activity elevated in a dose-dependent manner in the group administered with 30 mg/kg to 100 mg/kg of the test compound.

EXAMPLE 3

Figure 3:
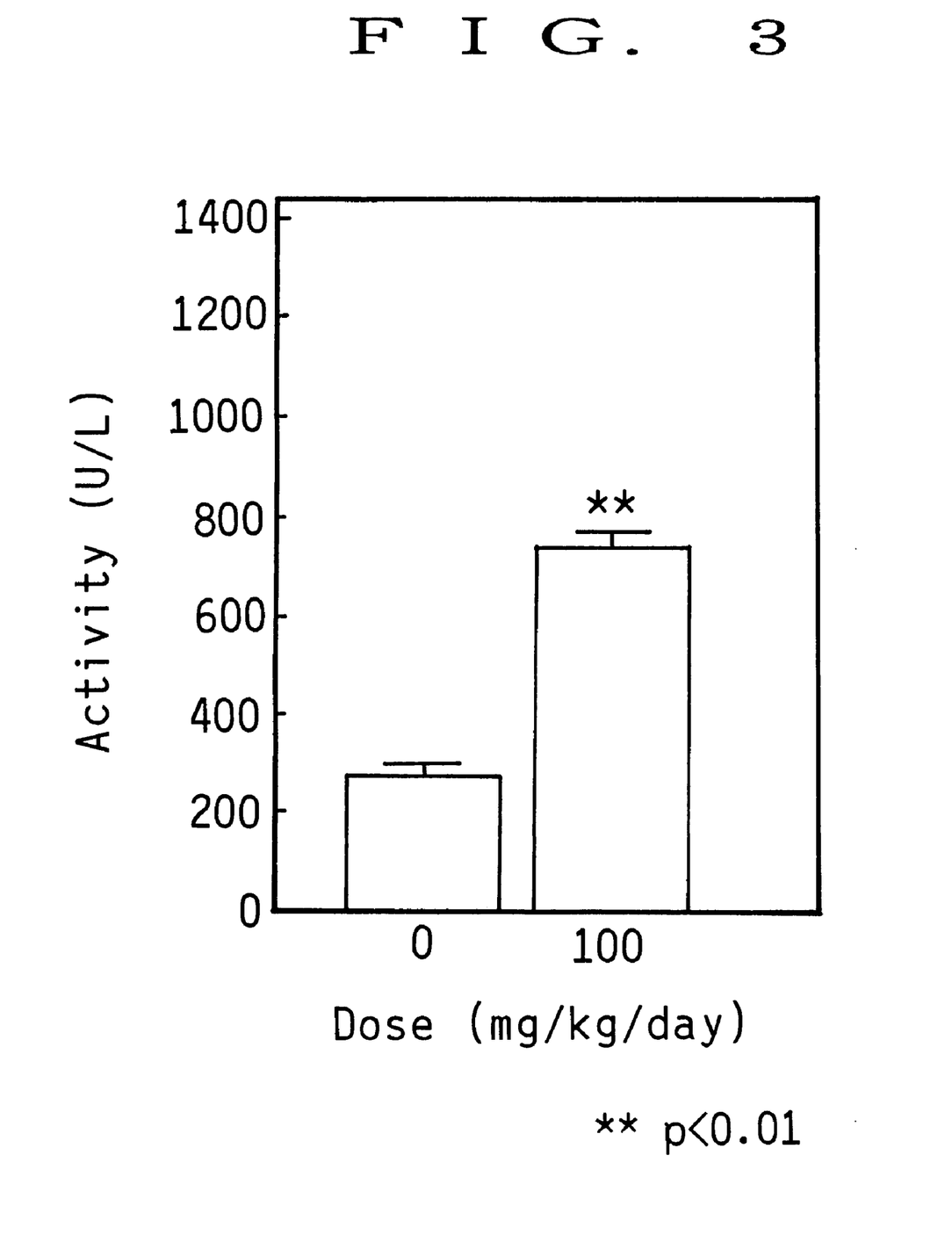
FIG. 3 shows the effects of the test compound (repeated oral administration for 7 days) on plasma cholinesterase activity.

Changes of Plasma Cholinesterase Activity After Repeated Administration for 7 Days To male SD rats (10 weeks of age, Japan Charles River, 4 per group) was orally administered, once a day for consecutive 7 days, (2S)-1-benzylaminocarbonyl-[(2S)-2-glycolylpyrrolidinyl]-2-pyrrolidinecarboxamide (100 mg/kg) suspended in 0.5% aqueous sodium carboxymethylcellulose solution (5 ml/kg). At 24 hours after the final administration, the rats were sacrificed in the same manner as in Example 1, whereby test samples were obtained. To the control group was orally administered 0.5% aqueous sodium carboxymethylcellulose solution (5 ml/kg). The respective cholinesterase activities are shown in FIG. 3. The cholinesterase activity increased 2.7 times as that of the control.

EXAMPLE 4

Figure 4:
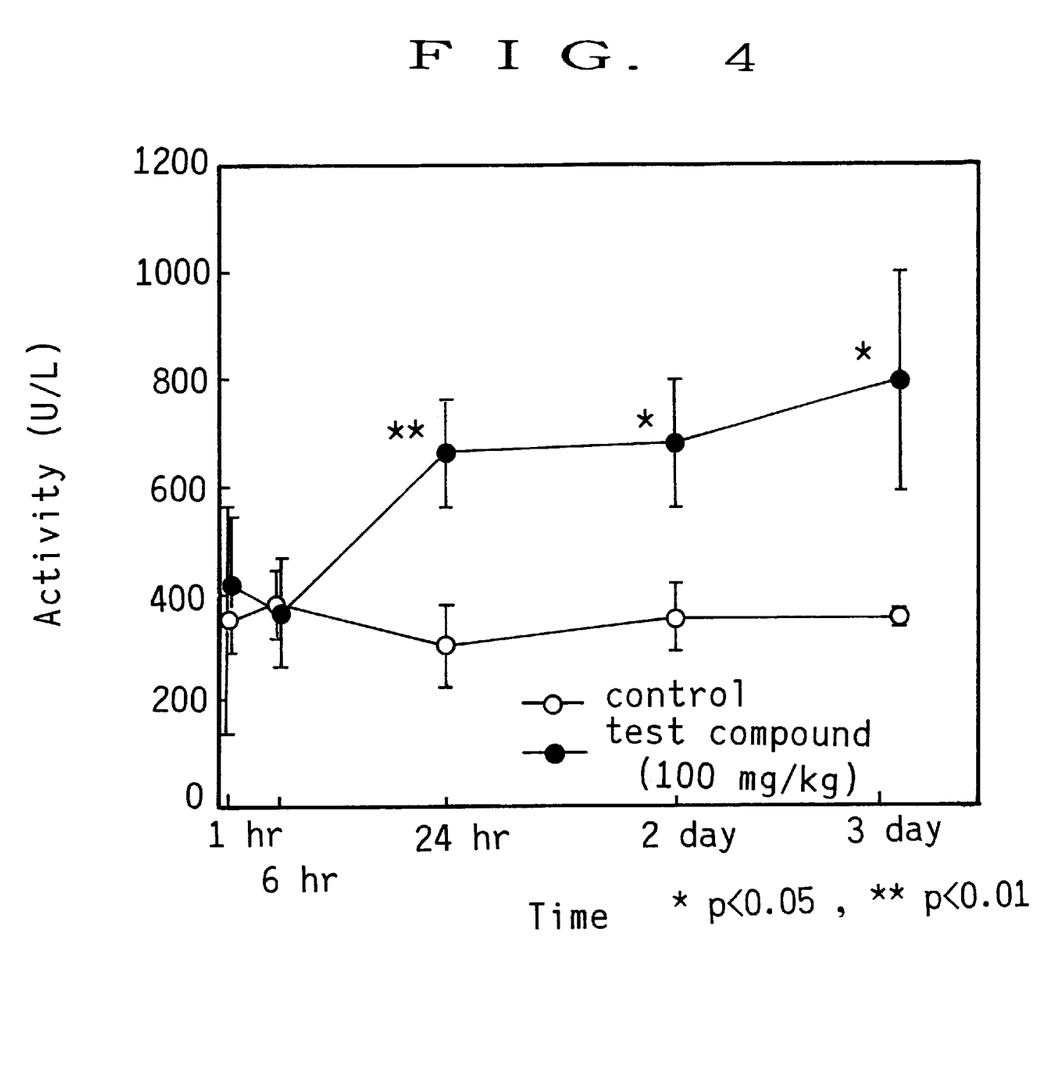
FIG. 4 shows the effects of the test compound (single intravenous administration) on plasma cholinesterase activity.

Time Course Changes in Plasma Cholinesterase activity After Single Intravenous Administration To male SD rats (6 weeks of age, Japan Charles River, 5 per group) was intravenously administered, from the tail vein, (2S)-1-benzylaminocarbonyl-[(2S)-2-glycolylpyrrolidinyl]-2-pyrrolidinecarboxamide (100 mg/kg) dissolved in physiological saline for injection (2.5 ml/kg). To the control group was intravenously administered, from the tail vein, physiological saline for injection (2.5 ml/kg). The rats were sacrificed in the same manner as in Example 1 at 1 hour, 6 hours, 24 hours, 2 days and 3 days later to obtain test samples, which were subjected to the determination of cholinesterase activity. The results are shown in FIG. 4. The cholinesterase activity started to increase from 24 hours postadministration and continued to increase with the passage of time for 3 days after administration.

EXAMPLE 5

Effects of Repeated Administration for 5 Days on the Metabolism of Cocaine (1) Sample Preparation To male ICR mice (10 weeks of age, Japan Clea, 11–15 per group) was orally administered, once a day for consecutive 5 days, (2S)-1-benzylaminocarbonyl-[(2S)-2-glycolylpyrrolidinyl]-2-pyrrolidinecarboxamide (100 mg/kg) dissolved in water (2.5 ml/kg). Control group was orally administered with physiological saline (2.5 ml/kg). At 5 minutes after the final administration of the test compound and saline, 20 mg/kg (10 ml/kg saline) of cocaine was intraperitoneally administered. The blood was taken by cervical incision at 30, 60, 120 and 240 minutes after administration. A small amount of eserine was added in advance into the blood sampling tube to prevent decomposition of cocaine after blood sampling. The blood was centrifuged immediately at 4° C. to give a serum. To each serum (0.2–0.4 ml) was added 200 ng of lidocaine as the internal standard. Then, cocaine and its metabolites (benzoylecgonine, ecgonine methylester and norcocaine) were extracted. The standard product of the metabolite was prepared by hydrolysis or demethylation of cocaine. The cocaine and its metabolite were extracted as follows. For deprotenization, 0.5 M $HClO_4$ (2 ml) was added to the serum containing with lidocaine, and the mixture was centrifuged at 3000 rpm for 10 minutes. The upper layer was washed with ethyl ether, and the aqueous layer was made alkaline with 1 M $NH_4OH$, which was followed by extraction with 7 ml of $CH_2Cl_2$/2-propanol (9:1). The solvent was removed from the resulting organic layer under nitrogen atmosphere, and the organic layer was treated with 220 μl of pentafluoropropionic anhydride (PFP)/2,2,2-trifluoroethanol (TFE)/ethyl acetate (10:2:10) at 80° C. for 30 minutes, which was followed by evaporation of the solvent under nitrogen atmosphere. To the obtained residue was added 80 μl of toluene/heptane/iso-amyl alcohol (75:20:5) and 50 pl of 0.5 M phosphate buffer (pH 8.5), and the mixture was admixed by stirring. Centrifugation gave an organic layer containing cocaine and its metabolites.

Figure 5:
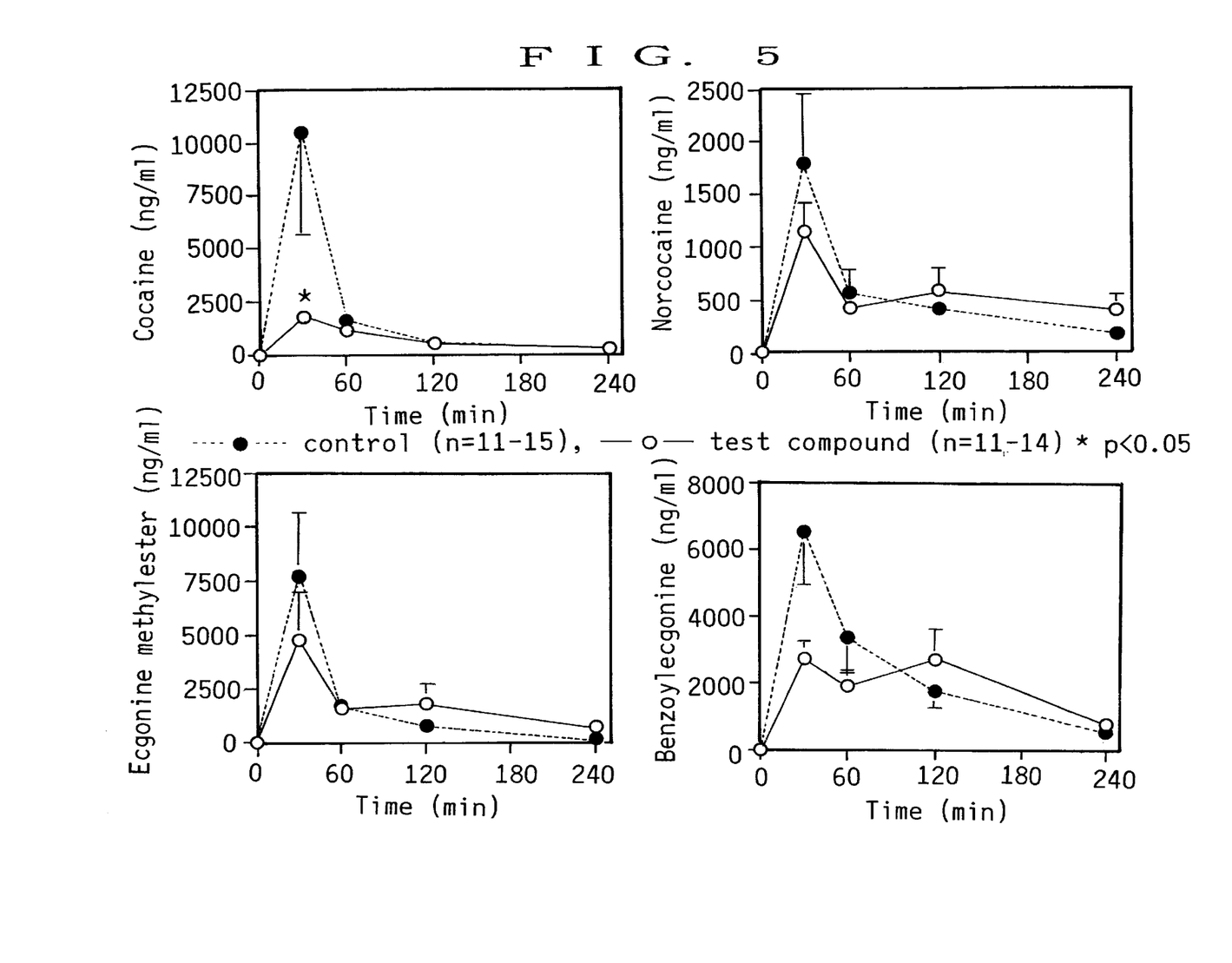
FIG. 5 shows the effects of the test compound (single oral administration) on the metabolism of cocaine.
Figure 6:
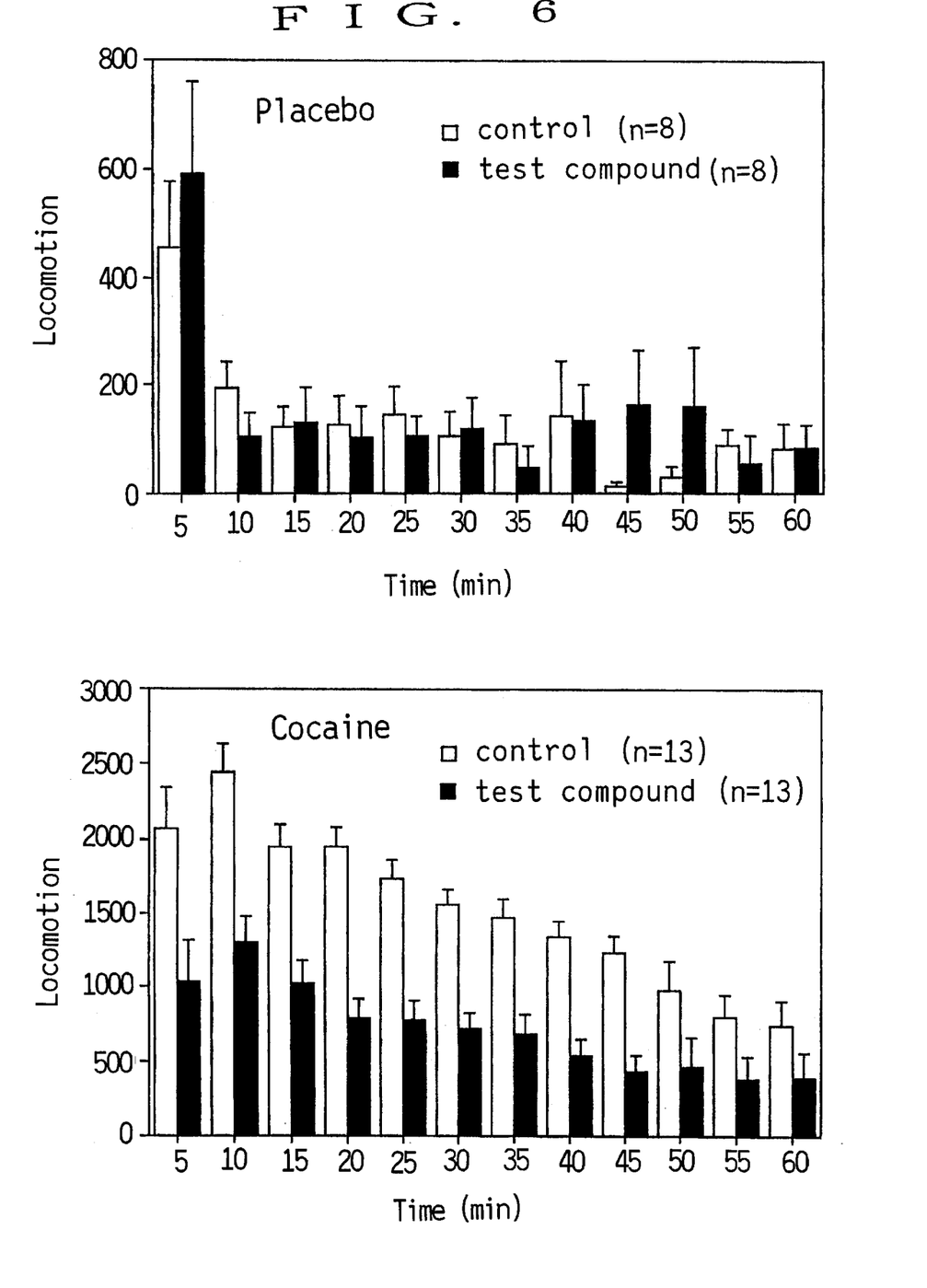
FIG. 6 shows the effects of the test compound (single oral administration) on cocaine-induced spontaneous locomotion.

The obtained organic layer (3 μl) was analyzed with a mass spectrometer directly connected to gas chromatography. The analysis conditions were as follows.

apparatus; HP 5890 II GC/HP 5972 MSD column; HP-5, 30 m×0.25 mm, 0.25 μm film temperature; injection port: 260° C., detector: 280° C.
   oven: 100° C. (1 min) programmed to 270° C. (5 min) at 20° C./min He pressure; constant flow after 25.2 psi for 0.5 min to 10.6 psi at 99.0 psi/min electron energy; 70 ev monitoring ions m/z 86: lidocaine
   m/z 250, 413: ecgonine-O-PFP, O-TFE
   m/z 182, 345: ecgonine methylester-O-PFP
   m/z 250, 371: benzoylecgonine-O-TFE
   m/z 182, 303: cocaine
   m/z 313, 105: norcocaine-N-PFP (2) Results The determination results of the contents of cocaine and its metabolites are shown in FIG. 5.

The concentration of non-metabolized cocaine of the group administered with (2S)-1-benzylaminocarbonyl-[(2S)-2-glycolylpyrrolidinyl]-2-pyrrolidinecarboxamide was significantly lower than that of the control group, as determined at 30 minutes after cocaine administration. While no statistic significance was observed, the benzoylecgonine concentration at 30 minutes after cocaine administration was also lower in the group administered with (2S)-1-benzylaminocarbonyl-[(2S)-2-glycolylpyrrolidinyl]-2-pyrrolidinecarboxamide.

EXAMPLE 6

Effects on Cocaine-induced Spontaneous Locomotion

To male ICR mice (10 weeks of age, Japan Clea, 13 per group) was orally administered, once a day for consecutive 5 days, (2S)-1-benzylaminocarbonyl-[(2S)-2-glycolylpyrrolidinyl]-2-pyrrolidinecarboxamide (100 mg/kg) dissolved in water (2.5 ml/kg). Saline (2.5 ml/kg) was orally administered to the control group. The treated mice were stabilized in a determination cage for 30 minutes, and cocaine was intraperitoneally administered according to Example 5. As placebo, saline was intraperitoneally administered instead of cocaine. The amount of spontaneous locomotion in one hour after administration was determined by SCANET (Toyo Industry) and detected by the "two-way analysis of variance with repeated measures on one factor" method.

The group treated with (2S)-1-benzylaminocarbonyl-[(2S)-2-glycolylpyrrolidinyl]-2-pyrrolidinecarboxamide showed a significant decrease by half of the increase in spontaneous locomotion induced by cocaine. A temporary increase in locomotion was found in the placebo groups, but no difference was found between the group treated with the test compound and the control group. The results were in harmony with the results obtained in Example 5, wherein serum cocaine concentration was lower than that of the control group for 1 hour after the administration of (2S)-1-benzylaminocarbonyl-[(2S)-2-glycolylpyrrolidinyl]-2-pyrrolidinecarboxamide.

As is evident from the foregoing Examples, a compound having a prolyl endopeptidase inhibitory activity significantly increases cholinesterase activity in the body. Thus, such compound can be beneficially used for the treatment of patients suffering from cocainism.

What is claimed is:

1. A method for treating cocainism comprising administering a pharmaceutically effective amount of (2S)-1-benzylaminocarbonyl-[(2S)-2-glycolylpyrrolidinyl]-2-pyrrolidinecarboxamide.

* * * * *